United States Patent [19]

Moghaddam

[11] Patent Number: 5,514,557

[45] Date of Patent: May 7, 1996

[54] METHOD AND KIT FOR DETECTING ANTIBODIES SPECIFIC FOR HLA AND/OR PLATELET GLYCOPROTEINS

[75] Inventor: Michael Moghaddam, Waukesha, Wis.

[73] Assignee: Genetic Testing Institute Inc., Brookfield, Wis.

[21] Appl. No.: 254,398

[22] Filed: Jun. 6, 1994

[51] Int. Cl.$^6$ ............................................. G01N 33/543
[52] U.S. Cl. ..................... 435/7.24; 435/7.21; 435/7.95; 435/975; 436/518
[58] Field of Search ............................. 435/7.21, 7.24, 435/7.95, 975; 436/518

[56] References Cited

U.S. PATENT DOCUMENTS

| | | | |
|---|---|---|---|
| 4,810,632 | 3/1989 | McMillan | 435/7 |
| 5,110,726 | 5/1992 | Ogden | 435/7.21 |
| 5,180,661 | 1/1993 | Brubaker | 435/7.21 |
| 5,231,025 | 7/1993 | Gralnick | 435/240.27 |
| 5,292,641 | 3/1994 | Pouletty | 435/7.24 |

OTHER PUBLICATIONS

Du, Xiaoping et al., "Ligands 'Activate' Integrin $\alpha_{IIb}\beta_3$ (Platelet GPIIb–IIIa)." *Cell;* 65: 409–16.

Dutcher, Janice P. et al., "Long–Term Follow–up of Patients With Leukemia Receiving Platelet Transfusions: Identification of a Large Group of Patients Who do not Become Alloimmunized." *Blood* 1981; 58: 1007–11.

Furihata, Kenichi et al., "On the Association of the Platelet–specific Alloantigen, Pen$^a$, with Glycoprotein IIIa." *J. Clin. Invest.* 1987; 80: 1624–30.

Galli, Monica et al., "Anti–Glycoprotein Ib/IX and IIb/IIIa Antibodies in Patients with Antiphospholipid Antibodies." *Thromb Haemost* 1994; 71: 571–5.

Herman, Jay J., "Platelet Antigens and Alloantibodies." *ASHI Quarterly* 1994; Spring: 4–6.

Kao, Kuo–jang et al., "Enzyme–Linked Immunoassay for Anti–HLA Antibodies—an Alternative to Panel Studies By Lymphocytotoxicity." *Transplantation* 1993; 55: 192–6.

Kiefel, V. et al., "The Br$^a$/Br$^b$ Alloantigen System on Human Platelets." *Blood* 1989; 73:2219–23.

Kieffer, Nelly et al., "Immunochemical Characterization of the Platelet–Specific Alloantigen Lek$^a$: A Comparative Study With the Pl$^{A1}$ Alloantigen." *Blood* 1984; 64: 1212–19.

Kunicki, Thomas J. et al., "The Immunogenicity of Platelet Membrane Glycoproteins." *Transfusion Medicine Reviews* 1987; 1:21–33.

Lyman, Suzanne et al., "Polymorphism of Human Platelet Membrane Glycoprotein IIb Associated With the Bak$^a$/Bak$^b$ Alloantigen System." *Blood* 1990; 75: 2343–48.

Parham, Peter, "Purification of Immunologically Active HLA–A and –B Antigens by a Serie of Monoclonal Antibody Columns." *J. Biol. Chem.* 1979; 254: 8709–12.

Phillps, David R. et al., "GPIIb–IIIa: The Responsive Integrin." *Cell* 1991; 65: 359–62.

Santoso, S. et al, "Identification of the Yuk$^b$ Allo–Antigen on Platelet Glycoprotein IIIa." *Vox. Sang.* 1987; 53: 48–51.

Van Der Schoot, C. Ellen et al., "Characterization of Platelet–Specific Alloantigens By Immunoblotting: Localization of Zw and Bak Antigens." *British Journal of Haematology* 1986; 64: 715–23.

*Primary Examiner*—David Saunders
*Attorney, Agent, or Firm*—Mark K. Johnson

[57] ABSTRACT

The present invention is directed to determining the presence of antibodies from a patient's blood which are specific for HLA Class I antigens and/or platelet glycoproteins. The invention provides for a method and kit for diagnosing platelet disorders in an easy to use format. The method and kit employ a solid support, such as microtiter plate wells, that are coated with the HLA and glycoprotein antigens. A sample of the patient's blood is added to the coated wells and allowed to react, then spectrophotometric detection of antibodies provides diagnostic quantitation.

15 Claims, No Drawings

METHOD AND KIT FOR DETECTING ANTIBODIES SPECIFIC FOR HLA AND/OR PLATELET GLYCOPROTEINS

BACKGROUND OF THE INVENTION

The present invention relates to a method and diagnostic kit for detecting platelet antibodies specific for human leukocyte antigens (HLA) class I as well as antibodies specific for platelet surface glycoproteins. These antibodies occur in the human population with an incidence of 30% or less causing platelet dysfunction. Since platelet dysfunction can occur for reasons other than the presence of the stated antibodies, their detection is important for patient diagnoses.

Blood obtained from different individuals has been found to have different antigenic and immune properties, to the extent that antibodies in the blood of one person may react with antigens on red blood cells or platelets in the blood of another individual. These antigens are often found on membrane glycoproteins present on the surface of the cell membranes. The antigens are also found on HLA which are also associated with platelets.

The blood platelet is one of the four primary elements that are important in maintaining hemostasis. It is a single cell that uses both its contents and cellular functions during the coagulation process. Platelets release mediators which promote a number of responses that are capable of initiating the hemostatic mechanisms and functions. These mediators may recruit other platelets to form an aggregated mass of coagulated platelets.

Patients who have normal or borderline platelet counts and a long bleeding time usually have a problem with platelet dysfunction. As the interaction of the platelet with vascular wall is important in determining the length of the bleeding time, vascular abnormalities can also mask platelet dysfunction in rare instances. Both hereditary and acquired types of platelet dysfunction may be seen clinically.

An immunological destruction of platelets can occur in patients with select hematologic disorders such as leukemia, systemic lupus erythematosus or other collagen-vascular diseases, viral infections, or in patients who have experienced alloimmunization because of a pregnancy or a transfusion. Therefore, it is important for physicians to properly diagnose and choose appropriate therapies for patients with bleeding problems caused by platelet dysfunction.

The presence of antibodies in the human circulation directed against foreign HLA signifies a unique immune state, termed HLA alloimmunity. This condition usually develops after direct, often unintentional exposure to a dose of foreign HLA antigens. The most common situation leading to HLA alloimmunity is pregnancy, because childbirth frequently exposes the mother to paternal HLA antigens carried on fetal blood cells. However, in medicine, blood component transfusion therapy frequently causes alloimmunization. Among mukitransfused subjects, the incidence of HLA alloimmunity ranges between 30 and 70%. See Schiffer et al., *Blood* 58:1007–11 (1981).

Neonatal alloimmune thrombocytopenic purpura (NATP) and posttransfusion purpura (PTP) are syndromes resulting from sensitization to platelet-specific alloantigens complexing with platelet glycoproteins. Autoimmune thrombocytopenia (AITP) represents a frequent kind of immune thrombocytopenia. This disease also manifests itself in the production of autoantibodies to platelet glycoproteins.

The diagnosis of these diseases in the clinical setting is often difficult. This is primarily because many factors may contribute to platelet dysfunction. Often, the individuals are receiving intense cancer therapy, or they may have received bone marrow or solid organ transplants. They may be patients who have suffered severe trauma or have recently had major surgery. Each of these clinical conditions is frequently accompanied by complications that reduce the effectiveness of platelet transfusion therapy. When platelet dysfunction symptoms appear, clinical distinction is frequently difficult if not impossible. Therefore, laboratory investigation complementing clinical diagnosis is particularly helpful.

SUMMARY OF THE INVENTION

It is an object of the present invention to provide an ELISA assay method having affinity-purified HLA Class I molecules, and platelet glycoproteins for the detection of platelet associated antibodies.

The method generally includes placing patient or donor serum into microtiter wells to be incubated. The wells have been coated with purified HLA Class I and platelet glycoproteins. The incubation of the serum with the potential antigens will allow an antibody-antigen complex to form. Unbound immunoglobulins are then removed by washing. An alkaline phosphatase labelled anti-human globulin reagent(s) (Anti-IgG/IgM/IgA) is added to the wells and then an enzyme buffer solution is added.

After an incubation period, microtiter wells are washed to remove any unbound reagent and enzyme substrate p-nitrophenyl phosphate (PNPP) is added to provide measurable color. After a timed incubation period, the reaction is stopped by a sodium-hydroxide solution and the optical density of the color is measured at a wavelength of 410 nm.

A kit is provided that comprises at least one microtiter plate with wells pre-coated with HLA Class I molecules and platelet glycoproteins. Also in the kit, a receptacle is provided for each of the anti-IgG/IgM/IgA reagent(s) and PNPP substrate. A receptacle may also be provided for each of the following: wash solutions, the sodium-hydroxide stop solution, the enzyme substrate buffer, a specimen diluent solution, a positive control and a negative control.

DETAILED DESCRIPTION OF THE PREFERRED EMBODIMENTS

The present invention is a solid phase ELISA assay method and kit which is used to detect Ig antibodies to platelet antigens. The method provides for the use of HLA Class I antigens and platelet glycoproteins GPIIb/IIIa, GPIb/IX, GP1a/IIa and GPIV.

Blood should be drawn from a donor or patient using aseptic technique and should be tested while still fresh to minimize the chance of obtaining false-positive or false-negative reactions due to improper storage or contamination of the specimen. Serum or plasma that cannot be tested immediately should be stored at 2°–8° C. for no longer than 48 hours or frozen. When stored or shipped, it should be separated from red cells. ACD or EDTA derived serum or plasma are suitable for this method.

All reagents should be at room temperature before using. Make a working wash solution by diluting a concentrated wash solution 1:10 with deionized water. The concentrated wash solution combines:

| | |
|---|---|
| NaCl | 88.0 g |
| KH₂PO₄ | 3.810 g |
| Na₂HPO₄ | 10.224 g |
| Tween 20 | 20.0 ml |
| NaN₃ | 5.0 g |

Prepare P-nitrophenyl phosphate or PNPP substrate by dissolving the freeze-dried crystalline powder provided with 1 ml of deionized water. Freeze the unused portion of PNPP solution for later use.

Add 250 µl of the working wash solution to all wells of a microtiter plate and let the solution stand for about 5–15 minutes, preferably 10 minutes. The microtiter plate should be a rigid flat-bottom microtiter plate. At least one well of the plate may contain HLA Class I attached to it's wall; at least one well may contain GPIIb/IIIa; at least one well may contain GPIb/IX; at least one well may contain GPIa/IIa; and, at least one well may contain GPIV. Each well could include one of the listed antigens or any combination, but, in the preferred embodiment, two wells are coated with each of the listed antigens. The working wash solution should then be decanted or aspirated from each well, inverted and blotted using absorbent material to remove any residual fluid.

The patient samples are diluted along with a negative control well and a positive control well. The dilution proceeds as follows:

a. Add 140 µl of a negative sample to 420 µl of a specimen diluent solution. The negative sample is normal blood type O serum with 0.1% sodium azide added as a preservative. The specimen diluent solution is a phosphate buffered saline (PBS) solution containing bovine serum albumin and mouse serum in the following amounts:

| | |
|---|---|
| KH2PO4 (diluted to 500 ml) | 34.02 g |
| Na2HPO4 (diluted to 500 ml) | 35.5 |
| NaCl | 8.8 g |
| NaN3 | 1.0 g |
| Tween 20 | 2.0 ml |
| Bovine Albumin (30%) | 33.4 ml |
| Patent blue stock | 1.2 ml |
| patent blue stock: | |
| 1.0 g of patent blue powder (dil. to 100 ml) | |
| 0.1 g of NaN3 | |
| Mouse serum | 5% | b. Add 50 µl of strong positive control sample (of antibodies specific for the glycoproteins listed above) to 150 µl of the specimen diluent solution. The strong positive serum control is serum strongly positive for platelet antigen-antibody reaction; it contains 0.1% sodium azide as a preservative.

c. Add 50 µl of weak positive control sample to 150 µl of the specimen diluent solution. The weak positive serum control is weakly positive for platelet antigen-antibody reaction; it also contains 0.1% sodium azide as a preservative.

d. Add 140 µl of patient serum or plasma to be tested to 420 µl of the specimen diluent solution.

Mix each dilution thoroughly.

Add 50 µl of each of the dilutions to appropriate wells in the microtiter plate. In the preferred embodiment 2 wells are reserved for each of the controls and 2 wells are reserved for each of the listed antigens. The plate is covered with a sealer and allowed to stand at room temperature for approximately 30 to 80 minutes; preferably 60 minutes. Alternatively, the plate may be incubated for about 20 to 40 minutes at 37° C.

Decant or aspirate the contents of each well after the standing or incubation time is complete. Add 200–300 µl of the working wash solution, then aspirate. Repeat this sequence twice more for a total of three washes. Invert the plate and blot on an absorbent material to remove any residual fluid. It is important to completely empty each well after each washing step and when washing is complete.

Dilute anti-human IgG, IgM, IgA 1:100 with the specimen diluent solution. Mix well. Add 50 µl of the diluted Ig solution to all of the prepared wells. Cover the plate with the plate sealer and allow the wells to stand at room temperature for about 30–80 minutes; preferably 60 minutes. Alternatively, the plate may be incubated for about 20–40 minutes at 30° C. After the appropriate standing or incubation time, repeat the last wash step. Add 100 µl of PNPP stock solution (prepared earlier) to 10 ml of a substrate buffer. The substrate buffer has the following ingredients:

| | |
|---|---|
| Diethanolamine | 48.5 ml |
| Distilled water | 421.5 ml |
| 1M HCl | 30.0 |
| MgCl₂.6H₂O | 50.0 mg |
| 100% NaN₃ | 1.0 ml |
| pH adjusted to 9.8 | |

Mix the stock solution and buffer completely and keep the resulting mixture away from direct light. This reagent should be used immediately after preparation.

Add 100 µl of the PNPP stock solution diluted with substrate buffer to each of the prepared wells. Allow the plate to stand for about 15–30 minutes. Standing time after the addition of PNPP is critical. Do not exceed the preferred time limit.

After the standing time is complete, add 100 µl of ELISA stopping solution (3M NaOH) to each of the prepared wells to stop the reaction. Then add 1001 µl of deionized water to one row of non-prepared wells to be used as blank controls.

The absorbance (OD) of each well should be measured at preferably 410 nm, using 490 nm as a reference wavelength. Perform this step within 30 minutes of stopping the reaction.

Test results indicating OD values equal to or greater than 2 times the value obtained for the mean measurement of the negative controls. The following test results were obtained from patients, some of whom are known positive (indicated by shading), and some are known negative (also indicated by shading); most of the patients were not known one way or the other, however, no unexpected results were obtained. The control numbers is the control mean multiplied by 2. Any number greater that the indicated control number shows a positive reaction for each group. The control number refers to the prior 7 patients.

| PATIENT | HLA CLASS I | GPIIb/IIIa | GPIbIX | GPIa/IIa |
|---|---|---|---|---|
| 1 | 0.226 | 0.899 | 0.081 | 0.125 |
| 2 | 0.187 | 0.697 | 0.070 | 0.144 |
| 3 | 0.105 | 0.465 | 0.071 | 0.101 |
| 4 | 0.490 | 0.157 | 0.101 | 0.156 |
| 5 | 0.822 | 0.122 | 0.107 | 0.124 |
| 6 | 0.436 | 1.302 | 0.102 | 0.177 |
| 7 | 1.013 | 0.113 | 0.101 | 0.210 |
| CONTROL | 0.312 | 0.270 | 0.198 | 0.266 |

| PATIENT | HLA CLASS I | GPIIb/IIIa | GPIbIX | GPIa/IIa |
|---|---|---|---|---|
| 1 | 0.124 | 0.039 | 0.015 | 0.053 |
| 2 | 1.082 | [0.102] | 0.019 | 0.048 |
| 3 | 0.166 | 0.256 | 0.035 | 0.103 |
| 4 | 0.244 | 0.117 | 0.013 | 0.042 |
| 5 | 0.322 | 1.061 | 0.042 | 0.110 |
| 6 | 0.083 | 0.102 | 0.041 | 0.058 |
| 7 | 0.389 | 0.350 | 0.052 | 0.078 |
| CONTROL | 0.202 | 0.100 | 0.082 | 0.130 |
| 1 | 0.594 | 0.062 | 0.230 | 0.025 |
| 2 | 1.124 | 0.096 | 0.017 | 0.037 |
| 3 | [0.092] | 0.082 | 0.012 | 0.015 |
| 4 | 1.006 | 0.023 | 0.005 | [0.312] |
| 5 | 0.042 | 0.013 | 0.001 | 0.021 |
| 6 | 1.290 | 1.035 | 0.169 | 0.693 |
| 7 | 0.056 | 0.046 | [0.014] | 0.038 |
| CONTROL | 0.124 | 0.054 | 0.082 | 0.142 |
| 1 | 0.054 | 0.034 | [0.001] | 0.017 |
| 2 | 0.496 | [0.040] | [0.024] | 0.030 |
| 3 | 0.202 | [0.040] | 0.011 | 0.052 |
| 4 | 0.831 | 0.802 | 0.014 | 0.015 |
| 5 | 0.056 | 0.032 | 0.004 | 0.022 |
| 6 | 0.054 | 0.101 | 0.007 | 0.032 |
| 7 | 0.039 | 0.035 | 0.011 | [0.605] |
| CONTROL | 0.124 | 0.056 | 0.020 | 0.050 |
| 1 | 0.073 | 0.036 | 0.000 | [1.192] |
| 2 | 0.304 | 1.359 | 0.000 | 0.072 |
| 3 | 0.085 | 0.021 | 0.000 | 0.053 |
| 4 | 0.033 | 0.004 | 0.000 | 0.020 |
| 5 | 1.364 | 0.136 | 0.087 | 0.122 |
| 6 | 1.996 | 0.104 | 0.439 | 0.059 |
| 7 | 0.870 | [0.091] | [0.016] | 0.068 |
| CONTROL | 0.146 | 0.088 | 0.000 | 0.136 |
| 1 | 1.131 | 0.023 | [0.010] | [0.354] |
| 2 | [0.162] | 0.723 | 0.003 | 0.048 |
| 3 | [0.097] | 0.025 | 0.003 | 0.065 |
| 4 | 0.030 | 0.000 | 0.000 | 0.017 |
| 5 | 0.239 | 0.771 | 0.000 | 0.035 |
| 6 | 0.034 | 0.000 | 0.000 | 0.026 |
| 7 | 0.052 | 0.010 | 0.006 | 0.042 |
| CONTROL | 0.130 | 0.054 | 0.006 | 0.142 |
| 1 | [0.505] | 1.818 | [0.033] | [0.104] |
| 2 | [0.136] | 0.108 | 0.010 | 0.029 |
| 3 | [0.195] | 0.906 | 0.016 | 0.058 |
| 4 | 0.085 | 0.027 | [0.006] | 0.037 |
| 5 | 0.925 | 0.040 | 0.012 | 0.112 |
| 6 | 0.086 | 0.072 | [0.021] | 0.077 |
| 7 | 0.128 | [0.075] | [0.037] | 0.079 |
| CONTROL | 0.152 | 0.090 | 0.026 | 0.100 |

Kit

The present invention also provides a diagnostic assay for detection of antibodies for platelet antigens in kit form. The kit typically includes the following items in amounts sufficient for at least one assay:

Solid support: a solid support having bound thereto one or more HLA Class I antigens and/or platelet glycoproteins that will specifically react with a human antibody. Preferably the solid support is a preformed microtiter plate having one or more HLA Class I antigens or platelet glycoproteins (GPIIb-IIIa, GPIb-IX, GpIa-IIa, GPIV) bound to a well surface.

A receptacle for each of the following: a concentrated wash solution; anti-human IgG/IgA/IgM antibodies in solution; positive serum control; negative serum control; PNPP; enzyme substrate buffer; specimen diluent solution; ELISA stopping solution. The kit also contains at least one plate sealer and at least one strip frame. Instructions for use are also included. By the term "instructions for use," it is meant a tangible expression describing the reagent concentration for at least one assay method, parameters such as the relative amount of reagent and sample to be admixed, maintenance time periods for reagent/sample admixtures, temperature, buffer conditions and the like.

What is claimed:

1. A method for detecting and identifying the presence of antibodies from a patient's blood specific for purified HLA which are differentiated from antibodies specific for purified platelet glycoproteins comprising:
   a. obtaining serum from the patients blood;
   b. placing the serum on a solid support having one well with the purified HLA attached thereto and another well with the purified platelet glycoproteins attached thereto;
   c. detecting the presence of the antibodies on the solid support;
   d. identifying the antibodies detected in step c.

2. A kit for detecting and identifying the presence of antibodies from a patient's blood specific for purified HLA which are differentiated from antibodies specific for purified platelet glycoproteins comprising:
   a. a solid support having one well with the purified HLA attached thereto and another well with the purified platelet glycoproteins attached thereto;
   b. a receptacle containing an enzyme label solution for detecting the presence of the antibodies and identifying the antibodies detected.

3. A kit as claimed in claim 2, wherein the purified platelet glycoproteins are selected from the group consisting of GPIIb/IIIa, GPIb/IX, GpIa/IIa, and GPIV.

4. A kit as claimed in claim 3, wherein the purified HLA is HLA Class I.

5. The method of claim 1 wherein the platelet glycoproteins are selected from the group consisting of GPIIb/IIIa, GPIb/IX, GpIIa/IIa and GPIV.

6. The method of claim 5 wherein the method identifies the presence of human antibodies specific for HLA Class I attached to a well and the platelet glycoproteins of claim 5, each attached to a well separate from each other and the HLA Class I.

7. The method of claim 6 wherein step c. essentially consists of measuring the quantity of a detectable label.

8. The method of claim 7 wherein the detectable label is alkaline phosphatase attached to an anti-human globulin selected from the group consisting of Anti-IgG, Anti-IgM and Anti-IgA.

9. The method of claim 8 wherein an enzyme substrate p-nitrophenyl phosphate (PNPP) provides measurable color.

10. A kit as claimed in claim 4 wherein the kit further comprises a receptacle containing a substrate to the label in solution which reacts with the label to produce a measurable color.

11. A kit as claimed in claim 10 wherein the label consists of an enzyme attached to an anti-human globulin selected from the group consisting of Anti-IgG, Anti-IgM and Anti-IgA.

12. A kit as claimed in claim 11 wherein the enzyme is alkaline phosphatase.

13. A kit as claimed in claim 12 wherein the substrate is an enzyme substrate p-nitrophenyl phosphate (PNPP) to provide a measurable color.

14. A kit as claimed in claim 13 wherein the solid support is a microtiter plate.

15. A kit as claimed in claim 14 wherein HLA Class I is attached to a well and the platelet glycoproteins of claim 4 are each attached to a well separate from each other and HLA Class I.

* * * * *

UNITED STATES PATENT AND TRADEMARK OFFICE
CERTIFICATE OF CORRECTION

PATENT NO. : 5,514,557
DATED : May 7, 1996
INVENTOR(S) : Michael Moghaddam

It is certified that error appears in the above-indentified patent and that said Letters Patent is hereby corrected as shown below:

Column 1, line 40, delete "erythematosis" and insert -- --erythematosus-- --; column 1, line 55, delete "mukitransfused" and insert -- --multi transfused-- --; column 1, line 66, delete "dinical" and insert -- --clinical-- --

Column 6, claim 5, line 3, "GpIIa/IIa" and insert -- --GpIa/IIa-- --.

Signed and Sealed this

Seventh Day of January, 1997

*Attest:*

BRUCE LEHMAN

*Attesting Officer*      *Commissioner of Patents and Trademarks*